United States Patent [19]

Johnson et al.

[11] Patent Number: 5,895,748
[45] Date of Patent: Apr. 20, 1999

[54] PANEL OF ANTIBODIES FOR DETECTING CADHERINS AND CATENINS IN TISSUES AND METHOD OF USING THE PANEL OF ANTIBODIES

[76] Inventors: Keith R. Johnson; Margaret J. Wheelock, both of 2674 Goddard Rd., Toledo, Ohio 43606; Alejandro Peralta Soler, 2414 Garrett Rd., Drexel Hill, Pa. 19026; Karen A. Knudsen, 150 Spring Lane, Philadelphia, Pa. 19128

[21] Appl. No.: 08/758,047

[22] Filed: Nov. 27, 1996

[51] Int. Cl.$^6$ ............... G01N 33/574; A61K 39/395
[52] U.S. Cl. ........................... 435/7.23; 424/130.1
[58] Field of Search ................ 424/130.1; 435/7.23

[56] References Cited

U.S. PATENT DOCUMENTS

| | | | |
|---|---|---|---|
| 4,828,991 | 5/1989 | Hanna, Jr. et al. | 435/68 |
| 5,539,096 | 7/1996 | Babai et al. | 536/24.3 |
| 5,597,725 | 1/1997 | Suzuki | 435/328 |

OTHER PUBLICATIONS

Geiger B. et al., Broad spectrum pan–cadherin antibodies, reactive with the C–terminal 24 amino acid residues of N–caderin. J. Cell Sci. 97:607–614, 1990.

*Primary Examiner*—Ponnathapura Achutamurthy
*Assistant Examiner*—Hankyez T. Park
*Attorney, Agent, or Firm*—MacMillan, Sobanski & Todd, LLC

[57] ABSTRACT

There is provided an antibody-based panel for detecting the cadherin family of proteins, the catenin family of proteins and the plaque family of proteins in tissues for the diagnosis and prognostic assessment of human tumors. The panel includes a set of antibody reagents, each antibody reagent is capable of recognizing a specific protein where the protein is a member of either the general cadherin family of proteins, the general catenin family of proteins or the general plaque family of proteins.

4 Claims, No Drawings

5,895,748

PANEL OF ANTIBODIES FOR DETECTING CADHERINS AND CATENINS IN TISSUES AND METHOD OF USING THE PANEL OF ANTIBODIES

FIELD OF THE INVENTION

The present invention relates to a panel for detecting cadherins and catenins in tissues and a method of using the panel. More particularly, the present invention relates to a panel of antibodies for detecting cadherins and catenins in tissues and a method of using the panel.

BACKGROUND OF THE INVENTION

Adhesion between cells is a feature of all multicellular organisms, including humans. One class of proteins that mediate adhesion between cells is the cadherin family of proteins. Cadherin is a general term that identifies a family of calcium-dependent cell-cell adhesion molecules consisting of several distinct proteins. Typically each cadherin molecule crosses the plasma membrane of a cell so that there is an extracellular portion of the cadherin protein as well as an intracellular portion.

On the outside surface of a cell, the extracellular domain of a cadherin protein interacts with the extracellular domain of a cadherin on the adjacent cell. These extracellular interactions contribute to holding neighboring cells together. Different types of cells, for example nerve cells and intestinal cells, may display different types of cadherin proteins on their surfaces.

On the inside surface of the cell membrane, the cytoplasmic domain of the cadherin protein interacts with a set of proteins called catenins or plaque proteins. The catenins or plaque proteins provide a bridge between the cadherin and the cell's cytoskeleton. In addition to the structural function, catenins may also play a role in signaling the cell. One type of signal may be produced when the extracellular cadherin domain interacts with a partner in an adjacent cell.

When a physician suspects that a patient has a tumor, it is typical for a piece of the affected tissue to be removed surgically and sent to a pathology laboratory for analysis and assessment. Typically, the tissue specimen is fixed in 10% formalin and delivered to the pathology laboratory where it is embedded in paraffin and sliced into sections which are processed for analysis in a number of ways (for example, with various stains as further described herein). The pathologist then examines the stained tissue section using microscopic methods. Distinct features of the cells in the tissue are revealed by these methods. The pathologist then classifies the tumors and assesses the patient diagnosis and prognosis based upon the histological characteristics of the tumor cells. More particularly, using established criteria, the pathologist evaluates what is seen in the sections. Most of the pathologist's information is derived from examination of these tissue sections. The results of the analyses are combined into a pathology report. If the tissue contains cancerous cells, the cancer is described in detail, the type of tumor is identified and its particular characteristics described. The characteristics stated in the report are those observed by the pathologist during the examination of the tissue sections. Depending upon the number and type of analytical procedures performed on the tissue sections, the pathologist will learn to varying extent the details that provide the basis for the diagnosis, for judging the tumor grade, and for predicting the patient prognosis.

The decision concerning how to process the tissue sections depends on common and routine practices in the laboratory, with considerations being given to the history of the sample. For example, it is common practice to stain sections with hematoxylin and eosin. Other types of staining may be called for when the pathologist suspects the tumor may be of a particular type. The decisions of how to process tissue sections are based upon the cumulative knowledge and the aggregate experiences of the pathology community. New processing procedures become routine pathology practice when they have been proven to be informative in diagnosis/prognosis and if they are easily incorporated into the standard operations of a pathology laboratory. Research laboratories, in contrast to clinical laboratories, typically identify new ways to examine tissues and then seek to demonstrate their ability in clinical situations.

Because of the relative subjectivity of the foregoing procedure, researchers and pathologists are constantly searching for more objective makers of tumor diagnosis and prognosis. As a result of those investigations, the number of antibodies that are used as tumor markers has steadily increased. However, pathologists and researchers do not yet have access to a comprehensive set of reagents that may be used as universal markers for the diagnosis and prognostic assessment of tumors.

One of the characteristic features of cancer cells is that, relative to their normal counterparts, their cell adhesion systems are different. One manifestation of their altered cell adhesion properties is that many cancers can become metastatic. Thus, it is of interest to determine the status of cell adhesion molecules in cancer cells.

An object of the present invention is to provide a panel for detecting cadherins, catenins or plaque proteins in tissues. Yet another object of the present invention is to provide a panel of antibodies for detecting cadherins, catenins or plaque proteins in tissues. Another object of the present invention is to provide an antibody-based panel for detecting cadherins, catenins or plaque proteins in tissues to assess tumors. Another object of the present invention is to provide antibodies to cadherins, catenins or plaque proteins and to provide their method of use in the diagnosis and prognosis of human cancers.

SUMMARY OF THE INVENTION

Briefly, according to the present invention there is provided an antibody-based panel for detecting the cadherin family of proteins, the catenin family of proteins and the plaque family of proteins in tissues for the diagnosis and prognosis of cancer. The panel includes a set of antibody reagents, each antibody reagent is capable of recognizing a specific protein where the protein is a member of either the general cadherin family of proteins, the general catenin family of proteins or the plaque family of proteins. In a preferred embodiment, the antibody-based panel includes one or more antibody reagents specific for detecting the cadherin family of proteins selected from the group consisting of E-cadherin, P-cadherin, N-cadherin, M-cadherin, R-cadherin, OB-cadherin, desmosomal cadherins and protocadherins and/or one or more antibody reagents specific for detecting the catenin family of proteins selected from the group consisting of α-catenin, β-catenin, plakoglobin, p120$^{cas}$isoforms and other plaque proteins, such as, vinculin, α-actinin, desmoplakin, plakophilin, and the like.

DETAILED DESCRIPTION OF THE PREFERRED EMBODIMENTS

The panel in accordance with the present invention may be used in the assessment and differential diagnosis of tumors in tissue. In a preferred embodiment, the tissue samples to be evaluated are formalin-fixed, paraffin-embedded tissue. However, it will be appreciated that the tissue samples may also be frozen tissue samples. For a more detailed discussion of the use of frozen tissue reference is made to the Journal of Human Pathology, 26:1363–1369 (1995), The Differential Expression of N-Cadherin and E-Cadherin Distinguishes Pleural Mesotheliomas From Lung Adenocarcinoms, Peralta Soler, A., et al., incorporated herein by reference. The panel may be used in the assessment and differential diagnosis of tumors in human tissue.

In the preferred embodiment, the panel includes a set of antibody reagents. Preferably, each antibody reagent recognizes a specific protein where the protein is a member of either the general cadherin family of proteins or the general catenin family of proteins. For example, the panel may include one or more antibody reagents specific for detecting the cadherin family of proteins including E-cadherin, P-cadherin, N-cadherin, M-cadherin, R-cadherin, OB-cadherin, desmosomal cadherins and protocadherins; and for detecting the catenin family of proteins including α-catenin, β-catenin, plakoglobin and p120$^{cas}$isoforms, and the like. Each antibody reagent included in the panel must recognize its specific cadherin or catenin in tissues that have been processed in accordance with standard methods well known in the pathology art.

It will be appreciated that other families may be included in the panel or certain members of the cadherin or catenin family may be excluded from the panel. Thus, the invention is not limited to the cadherin and catenin proteins listed above, but can be practiced with other proteins and other families of proteins associated with the cadherin and catenin family of proteins. For example, the invention may be practiced with the plaque family of proteins, such as, vinculin, α-actinin, desmoplakin, plakothilin and the like.

A reduction in cadherin expression as well as functional alterations such as tyrosine phosphorylation, decrease cell-cell adhesion and are associated with tumor progression. Thus cadherins, and their associated proteins, the catenins, are used as prognostic indicators of tumor aggressiveness. It is believed that when present, cadherin expression in tumors may also be used to trace the histogenetic origins of the tumor cells, and serve as differential diagnosis markers between neoplasms of similar morphology but different histogenesis.

The invention will be further clarified by a consideration of the following examples, which are intended to be purely exemplary of the invention.

EXAMPLE 1

"The differential expression of N-cadherin and E-cadherin distinguishes pleural mesotheliomas from lung adenocarcinomas"

Monoclonal antibodies against α- and β-catenin were prepared in Balb/c mice by injecting subcutaneously purified maltose binding protein/catenin fusion proteins. Spleen lymphocytes were fused with myeloma cells P37X63Ag8.653 and SP2/O-AG14. Clones were assayed by immunoblot analysis and the binding sites of the monoclonal antibodies were mapped. Nested cDNAs were sequenced and the monoclonal anti-α-catenin (1G5 MAb) bound to a domain between amino acids 135 and 226 and the anti-β-catenin (12F7 MAb) recognized a site between amino acids 112–134. Mice were injected with a cytoplasmic fragment of the human N-cadherin expressed and purified using New England BioLab's pMAL expression system as well known in the art.

Western Immunoblots

Anti-N-cadherin (13A9 MAb) and anti-E-cadherin (E9 MAb) monoclonal antibodies were tested by Western immunoblotting in HeLa cells and the human JAR-PR497 choriocarcinoma cell line (American Type Culture Collection). Polyacrylamide slab gel electrophoresis in the presence of SDS (SDS-PAGE) was performed using an 8% resolving gel and a 3.5% stacking gel (Bio Rad, Richmond, Calif.). SDS-PAGE resolved proteins from HeLa and JAR cell extracts were transferred electrophoretically to nitrocellulose, blocked with 3% bovine serum albumin, and incubated with anti-N-cadherin 13A9 MAb, anti-E-cadherin E9 MAb, nonimmune supernates or no primary antibody. The samples were incubated with the appropriate species specific alkaline phosphatase conjugated secondary antibodies (Promega, Madison, Wis.) and nitro-blue-tetrazolium and 5-bromo-4-chloro-3-indolyl phosphate substrates (NBT/BCIP).

Tumors and Cell Lines

Frozen tumor tissues from 19 pleural mesotheliomas and 16 lung adenocarcinomas were used in the study.

Immunofluorescence and Immunohistochemistry

Frozen sections of tumor tissues fixed with acetone at −20 C. for 10 minutes were exposed to 10% normal goat serum for 30 minutes and incubated with anti-N-cadherin 13A9 MAb, anti-E-cadherin E9 MAb, anti-α-catenin 1G5 MAb or anti-β-catenin 12F7 MAb, overnight at 4° C. in a humid chamber. Immunofluorescence (IF) was performed using species-specific secondary antibodies conjugated to either rhodamine or fluorescein (Jackson ImmunoRes. Laboratory, West Grove, Pa.). Immunohistochemistry was performed by the avidin-biotin method (Vectastin, Vector Lab., Burlingame, Calif.). Cultured cells grown on multiple chamber slides were fixed in acetone at −20° C. and stained by IF as described. The staining was scored based on the semi-quantitative assessment of the intensity staining, distribution patterns of staining (plasma membrane versus cytoplasm) and number of positive and negative tumor cells. Nonneoplastic stromal cells and areas of extensive necrosis or hemorrhage were not included. Tumors were classified as follows: negative (−); with less than 10% of the cells with cytoplasmic staining (−+); with 10% to 30% of the cells with weak plasma membrane staining (+); with 70% to 80% of the cells with strong plasma membrane staining (++); tumors with almost 100% of the cells with strong plasma membrane staining (+++).

Results

The anti-N-cadherin (13A9 MAb) and anti-E-cadherin (E9 MAb) monoclonal antibodies were tested by Western immunoblotting in human cells using extracts of HeLa cells (a human cervical carcinoma cell line) that expresses N-cadherin, and the human JARPR497 choriocarcinoma cell line, known to express E-cadherin. SDS-PAGE-resolved proteins from HeLa cell extracts and JAR cells were incubated with anti-N-cadherin 13A9 MAb, anti-E-cadherin E9 MAb), nonimmune supernatants or no primary antibody and the appropriate species-specific alkaline phosphatase-conjugated secondary antibodies and nitro-blue-tetrazolium and 5-bromo-4-chloro-3-indolyl phosphate substrates (NBT/BCIP). The results showed a single 135 KDa band corresponding to N-cadherin in the HeLa cell extract, and a single 120KDa band corresponding to E-cadherin in the JAR cell extract.

It was also observed that the distribution of IF staining of N-cadherin, α-catenin, and β-catenin in an epithelioid mesothelioma was identical to that seen in the JAR and HeLa cells, being noticeably abundant on the lateral sides of the plasma membranes, at the sites of contact between cells. N-cadherin and catenins were more segregated in the lateral plasma membrane domain in epithelioid mesothelioma tumor cells than in the spindle fibroblast-like cells of sarcomatous mesotheliomas.

Table 1 below shows the expression of N-cadherin, E-cadherin, α-catenin and β-catenin in mesotheliomas and lung adenocarcinomas. Both IF and immunohistochemistry showed that all mesotheliomas, regardless of their histological type expressed abundant N-cadherin. In some mesotheliomas, a weak, mostly cytoplastic expression of E-cadherin was observed above the background in a small percentage of cells. In contrast, all adenocarcinomas expressed E-cadherin. The variable intensity of E-cadherin staining did not correlate with the histological grade of the adenocarcinomas suggesting that alterations in the function rather than in the expression of the cadherin/catenin complex may have played a role in the aggressiveness of those tumors. N-cadherin was absent in 13 adenocarcinomas and weakly expressed in the cytoplasm of a small percentage of tumor cells in 3 adenocarcinomas. The data showed that the expression of N-cadherin versus E-cadherin were differential markers of mesothelioma versus lung adenocarcinoma, respectively. The catenins were expressed in both types of tumors with variable intensity and cellular distribution.

TABLE 1

| Case | Diagnosis | N-cadherin | E-cadherin | α-catenin | β-catenin |
|---|---|---|---|---|---|
| 1 | P mesoth epith | +++ | − | +++ | NP |
| 2 | P mesoth epith | +++ | −+ | +++ | NP |
| 3 | P mesoth biphas | ++ | − | +++ | ++ |
| 4 | P mesoth biphas | +++ | − | +++ | NP |
| 5 | P mesoth epith | +++ | −+ | +++ | NP |
| 6 | P mesoth biphas | +++ | − | +++ | NP |
| 7 | P mesoth biphas | ++ | −+ | | NP |
| 8 | P mesoth biphas | +++ | − | +++ | NP |
| 9 | P mesoth biphas | ++ | −+ | | NP |
| 10 | P mesoth biphas | +++ | − | +++ | +++ |
| 11 | P mesoth epith | +++ | − | +++ | NP |
| 12 | P mesoth sarcom | ++ | − | NP | + |
| 13 | P mesoth sarcom | +++ | − | +++ | +++ |
| 14 | P mesoth biphas | +++ | − | +++ | +++ |
| 15 | P mesoth sarcom | +++ | − | +++ | +++ |
| 16 | P mesoth epith | +++ | −+ | +++ | +++ |
| 17 | P mesoth biphas | +++ | + | +++ | NP |
| 18 | P mesoth biphas | +++ | −+ | +++ | NP |
| 19 | P mesoth epith | ++ | − | NP | ++ |
| 1 | L edenoca | − | ++ | +++ | NP |
| 2 | L pd adenoca | − | +++ | +++ | NP |
| 3 | L papil adenoca | − | +++ | +++ | NP |
| 4 | L adenoca | − | +++ | +++ | NP |
| 5 | L pd adenoca | − | ++ | +++ | NP |
| 6 | L adenoca | − | ++ | +++ | NP |
| 7 | L pd adenoca | − | ++ | NP | +++ |
| 8 | L adenoca | −+ | +++ | NP | +++ |
| 9 | L adenoca | −+ | +++ | NP | +++ |
| 10 | L adenoca | −+ | +++ | NP | +++ |
| 11 | L alveolar ca | − | +++ | NP | NP |
| 12 | L adenoca | − | ++ | NP | NP |
| 13 | L adenoca | − | + | NP | NP |
| 14 | L adenoca | − | + | NP | NP |
| 15 | L adenoca | − | + | NP | NP |
| 16 | L P adenoca | − | +++ | +++ | +++ |

In the foregoing table, the abbreviations are as follows: P-pleural, mesoth-mesothelioma, epith-epithelioid, biphas-biphasic, sarcom-sarcomatous, L-lung, pd-poorly differentiated, adenoca-adenocarcinoma, papil-papillary, ca-carcinoma, NP-not performed.

EXAMPLE 2

"Differential expression of N-cadherin in pleural mesotheliomas and E-cadherin in lung adenocarcinomas in formalin-fixed, paraffin-embedded tissues"

The utility of N-cadherin and E-cadherin antibodies for distinguishing pleural mesotheliomas from lung adenocarcinomas was confirmed in routinely processed tissues.

Antibodies

The generation of the cadherin specific antibodies has been described in Knudsen KA, et al., Interaction of α-actinin with the cadherin/catenin cell-cell adhesion complex via a-catenin, Journal Cell Biology, 130:67–77 (1995) and Wheelock MJ, et al., the soluble GP80 fragment of cell CAM 120/80 disrupts cell-cell adhesion, Journal Cell Biochemistry 34:187–202 (1987), incorporated herein by reference. Other antibodies used to characterize tumor in this study included: monoclonal CEA (Biogenex, San Raamon, Calif.); pan-keratin cocktail (Bio Tek, Santa Barbara, Calif.); cytokeratin 7 (Dako, Carpenteria, Calif.); cytokeratin 20 (Dako); monoclonal EMA (Dako): vimentin (clone V9, Dako); CD15 (LeuM1, becton Dickinson); actor VIII (Dako); CD34 (Dako); CD57 (clone Leu7, Becton Dickinson); NSE (Dako); muscle specific actin (HHF35, BioTek); pan-cadherin antibody (Sigma, St. Louis, Mo.). Only the results of the cadherin expression are discussed below.

Case Selection

Cases from 1988–1996 were identified from the files of the Tumor Registry at The reading Hospital and Medical Center. The H&E sections and original IHC studies (when performed) were reviewed by two surgical pathologists to confirm the original histologic diagnosis. A total of 28 cases were retrieved including 14 mesotheliomas and 14 adenocarcinomas. One case originally diagnosed as mesothelioma was excluded from analysis. This tumor had a spindle cell pattern with an extensive vascular network, and expressed vimentin but was negative for all other antigens including pan-keratin, EMA, CD34, factor VIII, CD57, and HHF35. Examination of this tumor by electron microscopy showed myofibroblastic but not mesothelial or epithelial differentiation. Together, these features supported the diagnosis of a hemangiopericytoma. The tumor had no detectable E-cadherin or N-cadherin expression and was also negative for the antigens detected by a pan-cadherin antibody.

Immunohistochemistry 5 micron sections from the paraffin embedded tumors were used for the studies. Antigen expression was enhanced by heat treatment of sections in a steamer with citrate buffer using methods described in Shi SR et al., Antigen retrieval technique: a novel approach to immunohistochemistry on routinely processed tissue sections, Cell Vision 2: 6–22 (1995), incorporated herein by reference. IHC was performed using an indirect method with DAB chromogen, employing standard protocols on an automated Biotek Techmate 1000 immunostainer. Appropriate positive and negative controls for the cases were included. Formalin fixed paraffin embedded sections of resected tumors, and cell blocks of pleural effusions were stained with antibodies specific for N-cadherin (13A9 MAb), and E-cadherin (E9 MAb). After exclusion of a hemangiopericytoma, tumors from 27 patients were studied, which included 13 cases of mesotheliomas, and 14 cases of adenocarcinoma. The amount of cadherin expression was quantified as follows: 0% expression, + up to 20% cells positive, ++21–50% of cells positive, +++ greater than 50% of cells positive.

Electron Microscopy

Tissues were obtained from the paraffin embedded blocks corresponding to the hemangiopericytoma and one micropapillary pleural mesothelioma which was negative for epitopes detected by N-cadherin antibody 13A9 and E-cadherin antibody E9. After deparaffinization, the tissue was fixed in osmium tetroxide, dehydrated with alcohols, and embedded in Epon. Thick sections were stained with toluidine blue and examined by light microscopy, after which thin sections were selected for examination by electron microscopy.

Results

N-cadherin is expressed in mesotheliomas and E-cadherin is expressed in adenocarcinomas. Because cadherins are homotypic adhesion proteins and mediate cell to cell interaction, their expression is localized to and most readily detected in the regions of cell to cell contact. In mesotheliomas, N-cadherin expression was present whereas E-cadherin expression was absent. In contrast, in adenocarcinomas the reciprocal pattern of staining was observed.

Of the 27 tumors analyzed, 24 showed exclusive expression of one but not the other cadherin. This included 12 of 13 mesotheliomas which were N-cadherin positive and E-cadherin negative and 12 of 14 lung adenocarcinomas were N-cadherin negative and E-cadherin positive. One lung adenocarcinoma was predominantly and extensively E-cadherin positive but showed some foci of tumor which were N-cadherin positive (Table 2 Case A13), and two cases which were negative for both cadherins (one adenocarcinoma and one mesothelioma, Table 2, cases A5 and M6).

The paraffin studies showed that N-cadherin expressing mesotheliomas included cases with pure epithelial pattern, sarcomatoid/spindle cell pattern and mixed/biphasic epithelial and sarcomatoid pattern. Importantly, N-cadherin expression was present in both the epithelioid and spindle cell regions of a biphasic mesothelioma.

In contrast, adenocarcinomas were E-cadherin positive with only one case showing focal expression of N-cadherin in a few cells with the vast majority of the tumor cells expressing E-cadherin (Table 2, case A13). The presence of focal E-cadherin expression in some cases of E-cadherin positive adenocarcinomas was also observed in Example 1.

The two cases that were negative for both N-cadherin and E-cadherin included one mesothelioma and one adenocarcinoma. The mesothelioma was a small micropapillary tumor positive for both cytokeratin and vimentin. Electron microscopy confirmed the mesothelial origin and presence of elongated microvilli in this tumor. The adenocarcinoma was a poorly differentiated tumor which invaded skeletal muscle of the adjacent chest wall. The lack of staining with N-cadherin and E-cadherin antibodies 13A9 and E9 may reflect the absence of cadherin proteins in these two tumors, or alternatively the loss of the specific epitopes recognized by the 13A9 MAb and E9 MAb. When these two tumors were examined further with a pan-cadherin antibody (Sigma), both the micropapillary mesothelioma and the poorly differentiated adenocarcinoma in skeletal muscle, showed positive reactions. This suggested that the two tumors expressed some type of cadherin, which was not recognized by 13A9 MAb and E9 MAb.

TABLE 2

| Case | Diagnosis | N-cadherin | E-cadherin |
| --- | --- | --- | --- |
| M1 Bx | meso, Ep | ++ | − |
| M2 Bx/CB | meso, Ep | ++ | − |
| M3 Bx/CB | meso, Ep | ++ | − |
| M4 CB | meso, Ep | ++ | − |
| M5 Bx/CB | meso, Ep/S | +++ | − |
| M6 Bx | meso, Ep | − | − |
| M7 Resection | meso, S | + | − |
| M8 Bx | meso, Ep | ++ | − |
| M9 CB | meso, Ep | ++ | − |
| M10 Bx | meso, Ep | ++ | − |
| M11 CB | meso, Ep | ++ | − |
| M12 Bx/CB | meso, Ep | +++ | − |
| M13 CB | meso, Ep | +++ | − |
| A1 CB | adeno | − | +++ |
| A2 CB | adeno | − | + |
| A3 Resection | adeno | − | ++ |
| A4 Resection | adeno | − | ++ |
| A5 Resection | adeno | − | − |
| A6 Resection | adeno | − | ++ |
| A7 Resection | adeno | − | ++ |
| A8 Resection | adeno | − | ++ |
| A9 Resection | adeno | − | ++ |
| A10 Resection | adeno | − | ++ |
| A11 Resection | adeno | − | ++ |
| A12 Resection | adeno | − | ++ |
| A13 Resection | adeno | − | ++ |
| A14 Resection | adeno | − | +++ |

In the foregoing table, the abbreviations are as follows: adeno-adenocarcinoma, Bx-biopsy, CB-cell block, Ep-epithelial, meso-mesothelioma, S-sarcomatoid.

As shown in Example 2, antibodies to N-cadherin and E-cadherin recognize formallin/paraffin resistant epitopes in mesotheliomas and lung adenocarcinomas, respectively. Thus, when N-cadherin and E-cadherin are used together as a panel, the diagnosis of pleural mesotheliomas and lung adenocarcinoms may be made with increased certainty.

EXAMPLE 3

"The expression of E-cadherin and N-cadherin in surface epithelial-stromal tumors of the ovary distinguishes mucinous from serous and endometrioid tumors"

Tissues and Antibodies

Routinely processed paraffin embedded tissues from 46 ovarian tumors, including serious, mucinous and endometrioid tumors were obtained from the archives of the Departments of Pathology of the Reading Hospital and Medical Center and The Lankenau Hospital. They included benign, borderline and malignant variants, the histotype of each tumor was established by standard pathological methods. An E-cadherin specific antibody (Transduction Labs, Lexington, Ky.) and N-cadherin specific antibody (13A9 MAb), see Knudsen, KA et al., Interaction of α-actinin with the cadherin/catenin cell-cell adhesion complex via α-catenin, Journal Cell Biology, 130:67–77 (1995), incorporated herein by reference, both mouse monoclonal antibodies were used. Western immunoblots were performed as described in extracts from JAR-PR497 choriocarcinoma and A431 carcinoma cells known to express E-cadherin and from HeLa and VA13 cells known to express N-cadherin (cells were from American Type Culture Collection) to confirm the specificity of the antibodies. The same E-cadherin (Transduction Labs) and N-cadherin (13A9) MAbs used for immunohistochemistry were applied to the Western immunoblots.

Immunohistochemistry

Immunostaining was performed in 5 micron-thick section using two antigen retrieval methods, steaming and pressure cooking. See Pasha T., et al., Nuclear antigen retrieval utilizing steam heat, Modern Pathology 8:167, (1995) and Miller R. T., et al., Heat induced epitope retrieval with a pressure cooker, Applied Immunochemistry, 3:190–193 (1995), incorporated herein by reference. After deparaffinization, sections were immersed in a citrate buffer (ChemMate Hier Buffer, BioTek Solutions, Inc., Santa Barbara, Calif.) and heated for 20 minutes in a Black and Decker steamer or in a pressure cooker. Sections were transferred to PBS, treated with normal goat serum for 30 minutes, incubated overnight at 4° C. in a humid chamber with N-cadherin 13A9 MAb conditioned supernate or with E-cadherin antibody diluted 1:50 in PBS. A standard immunohistochemical avidin-biotin method was applied following the manufacturers instructions (vectastin, Vector Lab, Burlingame, Calif.). The semiquantitative evaluation of the immunohistochemistry was performed in sections treated with the steam based antigen retrieval to maximize the consistency of the immunostaining of the different tumors.

Results

Western immunoblots confirmed previous results shown in Example 2 and showed that the e-cadherin MAb detected a 120 KDa band in the JAR-PR497 and the A431 cells, and the N-cadherin MAb detected a 135 KDa band in the VA13 and HeLa cells, with negligible background, indicating the specificity of the antibodies. Immunohistochemical staining of paraffin sections were performed with or without antigen retrieval methods for comparison of sensitivity and specificity of the immunostaining. Both steaming and pressure cooking antigen retrieval methods similarly enhanced the intensity of the specific immunostaining without generating non-specific background. Semiquantitative evaluation of the staining is shown in Table 3.

E-cadherin was expressed in all serous and endometrioid tumors. In both serous and endometrioid tumors the staining was generally restricted to areas of cell-cell contact. N-cadherin was also expressed in all serous and endometrioid tumors although in endometrioid tumors the staining was generally less intense and more cytoplasmic than in serous tumors. In addition, the plasma membrane straining of N-cadherin was occasionally restricted to a limited number of cells in endometrioid tumors. All mucinous tumors, both of enteric and Mullerian type, regardless of their degree of malignancy and differentiation, had intense staining of E-cadherin. In striking contrast, N-cadherin was absent in all mucinous tumors. The distribution of N-cadherin and E-cadherin in serous and endometrioid tumors was in most cases at the plasma membrane with the highest intensity in areas of contact between tumor cells. In a minority of serous and endometrioid tumors the N-cadherin staining was diffuse in the cytoplasm, suggesting defects in the adhesive properties of the tumor cells. The plasma membrane versus cytoplasmic staining patterns, however, did not correlate with the degree of differentiation of the tumors, as some poorly differentiated tumors had well defined plasma membrane staining. Mucinous tumors showed a striking and characteristic pattern of E-cadherin staining, with high intensity on the basolateral membranes and very low or absent staining on the apical membranes indicating preservation of cell polarity. Psammoma bodies found occasionally in serous tumors, stained positively for both E-caderin and N-cadherin suggesting a cellular origin for these structures.

TABLE 3

| Case | Diagnosis | E-cadherin | N-cadherin |
|---|---|---|---|
| 1 | serous cystadenoma | + | + |
| 2 | serous cystadenoma | +@ | + |
| 3 | serous cystadenoma | + | + |
| 4 | serous cystadenoma with papillae | + | + |
| 5 | serous cystadenoma/endometrioma | + | + |
| 6 | papillary serous cystadenoma, borderline | + | + |
| 7 | papillary serous cystadenoma, borderline | + | + |
| 8 | papillary serous cystadenoma, borderline | + | + |
| 9 | papillary serous cystadenoma, borderline | + | + |
| 10 | papillary serous cystadenocarcinoma, grade III | + | +@ |
| 11 | papillary serous cystadenocarcinoma, grade II | + | + |
| 12 | papillary serous cystadenocarcinoma, grade III | + | + |
| 13 | papillary serous cystadenocarcinoma, grade I | + | + |
| 14 | papillary serous cystadenocarcinoma, grade II | + | + |
| 15 | papillary serous cystadenocarcinoma, grade III | + | + |
| 16 | papillary serous cystadenocarcinoma, grade III | + | + |
| 17 | papillary serous cystadenocarcinoma, grade III | + | +* |
| 18 | papillary serous cystadenocarcinoma, grade I | + | + |
| 19 | papillary serous cystadenocarcinoma, grade III | + | +* |
| 20 | papillary serous cystadenocarcinoma, grade III | + | + |
| 21 | papillary serous cystadenocarcinoma, grade II | + | + |
| 22 | papillary serous cystadenocarcinoma, grade III | + | + |
| 23 | papillary serous | + | + |

TABLE 3-continued

| Case | Diagnosis | E-cadherin | N-cadherin |
|---|---|---|---|
|  | cystadenocarcinoma, grade II |  |  |
| 24 | papillary serous cystadenocarcinoma, grade I | + | + |
| 25 | papillary serous cystadenocarcinoma, grade II | + | +* |
| 26 | endometrioma | + | −+# |
| 27 | endometrioma | + | + |
| 28 | endometrioma | +@ | + |
| 29 | mixed endometrioid/serious carcinoma, grade III | + | + |
| 30 | endometrioid adenocarcinoma, with mucus, grade II | + | +* |
| 31 | endometrioid adenocarcinoma, grade I | + | +# |
| 32 | mucinous cystadenoma, enteric | + | − |
| 33 | mucinous cystadenoma, mullerian | + | − |
| 34 | mucinous cystadenoma, mullerian | + | − |
| 35 | mucinous cystadenoma, borderline, enteric | + | − |
| 36 | mucinous cystadenoma, borderline, enteric | + | − |
| 37 | mucinous cystadenoma, borderline, mullerian | + | − |
| 38 | mucinous cystadenoma, borderline, enteric | + | − |
| 39 | mucinous cystadenoma, borderline, enteric | + | − |
| 40 | mucinous cystadenoma, borderline, mullerian | + | − |
| 41 | mucinous cystadenocarcinoma, enteric | + | − |
| 42 | mucinous cystadencarcinoma, grade II, enteric | + | − |
| 43 | mucinous cystadenocarcinoma, grade II, enteric | + | − |
| 44 | mucinous cystadenocarcinoma, grade III, enteric and metastasis in gallbladder | + | − |
| 45 | mucinous cystadenocarcinoma, grade III, enteric and endometriosis | + | + |
| 46 | mucinous cystadenocarcinoma, grade III, enteric | + | − |

In the foregoing table, the tumors were classified as grade I (well differentiated), grade II (moderately differentiated) and grade III (poorly differentiated); *—groups of cells with positive plasma membrane staining, other negative. #—weak cytoplasmic staining in a minority of cells @—cytoplasmic but not plasma membrane staining.

As shown in Table 3, the differential expression of N-cadherin distinguishes mucinous tumors from serous and endometrioid tumors of the ovary. In addition, the expression of both E-cadherin and N-cadherin in serous and endometrioid tumors traces their origin to the surface epithelium of the ovary, an epithelial tissue of mesodermal origin. The absence of N-cadherin in all mucinous tumors suggests an origin different than the ovarian epithelium. However, because the expression of cadherins can be reduced in some tumors as the cells dedifferentiate and lose their resemblance to their putative cells of origin, it is believed that the absence of N-cadherin in mucinous tumors may represent post transformation selective protein loss rather than an indication of histogenesis. N-cadherin was absent in mucinous tumors of both enteric and Mullerian type, regardless of the degree of differentiation, including benign cystadenoma, borderline tumors, and invasive and metastatic carcinomas. This suggests that the absence of N-cadherin does not result from the loss of the molecule as a consequence of tumor progression, but is rather a feature characteristic of the cells of origin of the tumor. Furthermore, the high E-cadherin expression observed in all mucinous tumors, even in invasive carcinomas, supports the premise of an heterotopic origin for ovarian mucinous tumors from a predominately E-cadherin expressing tissue. Distinguishing these ovarian tumor types based on cadherin expression helps to better define the origin of the neoplasms and aids in the differential diagnosis of serous and endometrioid tumors with secretory and mixed patterns as well as undifferentiated carcinomas.

The documents and patent referred to herein are hereby incorporated by reference.

Having described presently preferred embodiments of the invention, it is to be understood that it may be otherwise embodied within the scope of the appended claims.

What is claimed is:

1. A method of using an anti-body based panel for the diagnosis and prognostic assessment of human tumors, comprising the steps of:

selecting a set of antibody reagents, each antibody reagent recognizing a specific protein in a paraffin-embedded section of a human tumor; and detecting the specific protein from a group selected from the group consisting of a general cadherin family of proteins, a general catenin family of proteins and a plaque family of proteins.

2. The method according to claim 1, wherein the panel includes one or more antibody reagents specific for detecting the cadherin family of proteins selected from the group consisting of E-cadherin, P-cadherin, N-cadherin, M-cadherin, R-cadherin, OB-cadherin, desmosomal cadherins and protocadherins.

3. The method of claim 1 wherein the anti-body based panel comprises monoclonal antibody reagents.

4. The method of claim 1 wherein the panel includes one or more antibody reagents specific for detecting the cadherin family of proteins selected from the group consisting of E-cadherin, P-cadherin, N-cadherin, M-cadherin, R-cadherin, OB-cadherin, desmosomal cadherins and protocadherins.

* * * * *